United States Patent [19]

Diem et al.

[11] 4,126,582

[45] Nov. 21, 1978

[54] MANUFACTURE OF SUPPORTED SILVER CATALYSTS

[75] Inventors: Hans Diem; Christian Dudeck; Werner Simmler, all of Ludwigshafen; Siegfried Marquardt, Bobenheim-Roxheim; Walter Stingl, Mannheim, all of Fed. Rep. of Germany

[73] Assignee: BASF Aktiengesellschaft, Ludwigshafen, Fed. Rep. of Germany

[21] Appl. No.: 824,524

[22] Filed: Aug. 15, 1977

[30] Foreign Application Priority Data

Sep. 1, 1976 [DE] Fed. Rep. of Germany ....... 2639342

[51] Int. Cl.$^2$ .............................................. B01J 23/50
[52] U.S. Cl. ..................................... 252/476; 427/304
[58] Field of Search ................. 252/463, 476; 427/304

[56] References Cited

U.S. PATENT DOCUMENTS

| 2,424,085 | 7/1947 | Bergsteinsson et al. | 252/476 X |
| 3,575,888 | 4/1971 | Long | 252/476 |
| 3,702,259 | 11/1972 | Nielsen | 252/463 X |

*Primary Examiner*—W. J. Shine
*Attorney, Agent, or Firm*—Keil, Thompson & Shurtleff

[57] ABSTRACT

An improved process for the manufacture of silver catalysts, in which the silver is applied to conventional dimensionally stable and chemically inert carriers, eg. alumina or quartz moldings, preferably by electroless deposition from silver salt solutions onto a great variety of surfaces acting as carriers, by the use of suitable reducing agents. In a particular embodiment, a uniform deposition of silver and a dense and well-adhering silver layer on the surface of the carrier are achieved by adding certain materials to the silver salt solutions.

9 Claims, No Drawings

MANUFACTURE OF SUPPORTED SILVER CATALYSTS

The manufacture of silver catalysts for various redox reactions, eg. for the manufacture of formaldehyde by dehydrogenating methanol, has been disclosed.

In the synthesis of formaldehyde by partial oxidation of methanol with a less than equivalent amount of air at an elevated temperature, a crystalline silver catalyst which consists of electrolytically purified silver granules of a defined particle size has hitherto been used. A contact furnace with a capacity of about 80 tones of formaldehyde per day requires, as the catalyst packing, from 400 to 450 kg of silver which, because of aging and sintering, must be replaced and reprocessed every 2 months. Hence, in addition to the actual packing, substantial amounts of silver must be kept in stock.

We have now found that supported silver catalysts which are very suitable for oxidation reactions are obtained when metallic silver is deposited as a dense well-adhering layer from silver solutions onto the carrier, by a direct electroless method using reducing agents, and without prior activation or sensitization of the carrier surface.

This process makes it possible to replace the crystalline solid silver catalyst by a silver-coated supported catalyst without having to accept adverse changes in the process conditions, or decreases in conversion or yield, of the dehydrogenation reaction. The advantages of the catalyst manufactured according to the invention are that in the catalytic processes in which this catalyst is employed the silver requirement can be reduced to 1/50 of the amount hitherto required, for the same yields and under the same process conditions.

Processes by which various surfaces, eg. plastics, can be coated with fine metal layers by an electroless method, through (reductive) deposition of the metals from the solutions of their salts, have previously been disclosed.

In one of these conventional methods, silver is formed by reduction from silver salt solutions in the cold, but after prior sensitization by adding complexing agents, eg. ammonia, and is precipitated in a finely divided form on the surfaces present. However, this conventional process suffers from the disadvantage that the coating process requires at least three steps, eg. sensitizing or activating the surface, rinsing and then silvering. In contrast, in the process according to the invention a dense and well-adhering silver layer is obtained direct, ie. without pretreating or sensitizing the surface.

Any materials which under the reaction conditions or at 800° C are still dimensionally stable and chemically inert may be used as the carriers. Rough-surfaced alumina, quartz moldings and commercial catalyst carriers based on α-alumina have proved particularly suitable for the manufacture of the catalyst.

Preferred reducing agents are hydrazine and hydrazine derivatives, glucose, formalin hydroxylamine.

A particularly advantageous embodiment is, for example, that compounds of the general formula

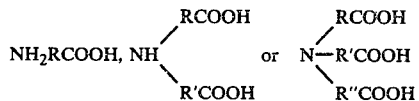

or salts thereof, where R, R' and R'' are identical or different hydrocarbon radicals, are added, individually or as mixtures, to the silver salt solution. These compounds are advantageously used in a proportion of from 0.02 to 0.3 mole per gram atom of silver present in the solution. Silver is used in the form of water-soluble salts, eg. silver nitrate.

The coating may in general be effected at from 0° to 100° C, preferably at from 10° to 30° C, at an alkaline, neutral or acid pH. The above compounds may already be added at the stage of preparing the silver salt solution.

To carry out the process of the invention it is possible, for example, to add a solution of hydrazine hydrate and distilled water in the ratio of 3:50 to the moldings to be used as carriers. The silver salt solution, comprising silver nitrate, nitrilotriacetic acid, ammonium hydroxide and distilled water in the weight ratio of, preferably, 5:0.2:5.2:95 or 25:1:26:475 is then added and the mixture is shaken gently. At reaction temperatures of from 10° to 30° C, the moldings are removed from the silver salt solution after reaction times of from 1 to 10 minutes, and are dried.

The advantages of the invention are that the coating of the catalyst carrier is effected without prior impregnation, activation or sensitization of the surface, whilst such treatments are necessary in the conventional processes of metal coating. Furthermore, firmly adhering and electrically conductive silver layers of any desired thickness can be produced with silver yields of more than 80%, based on the silver employed. The process of the invention also avoids poisoning of the catalyst which may result from activation with foreign metals.

The Example which follows describes the manufacture of a catalyst for the synthesis of formaldehyde from methanol.

EXAMPLE

The carrier used consists of porcelain beads of size 1–2 mm, which have a tap density of 2.0 kg/l and a conductivity of $<2.10^{-5}$ S.

50 ml of distilled water and 3 ml of analytical-grade 100% strength hydrazine hydrate are added to 52.8637 g of these beads. To this mixture are added 100 ml of a silver solution comprising 50 g of $AgNO_3$, 1.5 g of nitrilotriacetic acid and 58 ml of 25% strength aqueous $NH_4OH$. The reaction is allowed to proceed for 3 minutes at 27° C, with gentle stirring. The supernatant liquid is then decanted and the silvered carrier is washed neutral with distilled water and then dried at 120° C. The weight of the silvered carrier is 55.7591 g.

mg of Ag/g of carrier: 54.7
thickness of silver layer: 5 μ
surface area: 0.9 m²/kg / catalyst
conductivity: 1.92 S The silver yield achieved in manufacturing the catalyst is 91%.

For comparable conversions and yields, this catalyst makes it possible to lower the amount of silver used in the ratio of 1:50 as compared to solid silver catalysts in the manufacture of formaldehyde.

We claim:

1. A process for the manufacture of supported silver catalysts in which metallic silver is deposited on a carrier as a dense, well-adhering layer which comprises the steps of:
    (a) contacting the carrier with a reducing agent wherein said carrier surface has not been subjected to prior activation or sensitization, and (b) treating the carrier from step (a) with a silver salt solution, said solution containing a water-soluble silver salt, ammonium hydroxide and at least one carboxylic acid amino compound of the formula

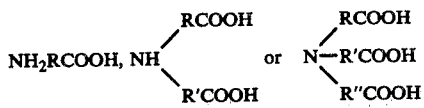

where R, R' and R'' are identical or different hydrocarbon radicals or their salts, whereby the silver is deposited by an electroless method in reaction times of from about 1 to 10 minutes.

2. A process as set forth in claim 1, in which any chemically inert material which is dimensionally stable at up to 800° C is used as the carrier.

3. A process as set forth in claim 1, in which hydrazine or a hydrazine derivative is used as the reducing agent.

4. A process as set forth in claim 1, in which the carboxylic acid amines are used in amounts of from 0.02 to 0.3 mole per gram atom of silver present in the solution.

5. A process as set forth in claim 1, in which the reducing agents are glucose, formalin or hydroxylamine.

6. A process as set forth in claim 1, in which the reaction temperature is from 0° to 100° C.

7. A process as set forth in claim 1, in which the reaction temperature is from 10° to 30° C.

8. A process as set forth in claim 1, in which the carboxylic acid amine is nitrilotriacetic acid.

9. A process as set forth in claim 1, in which the reducing agent is added in aqueous solution.

* * * * *